United States Patent
Connelly et al.

(10) Patent No.: US 7,470,248 B1
(45) Date of Patent: Dec. 30, 2008

(54) METHODS AND APPARATUS FOR VISUALLY DISTINGUISHING OCCLUSION ASSEMBLIES OF A SHUNT

(75) Inventors: Ryan H. Connelly, Beverly, MA (US); Stephen McCartin, Chelmsford, MA (US); David McDonald, Medway, MA (US)

(73) Assignee: LeMaitre Vascular, Inc., Burlington, MA (US)

( * ) Notice: Subject to any disclaimer, the term of this patent is extended or adjusted under 35 U.S.C. 154(b) by 436 days.

(21) Appl. No.: 10/998,688

(22) Filed: Nov. 29, 2004

(51) Int. Cl.
*A61M 5/00* (2006.01)
*A61M 29/00* (2006.01)

(52) U.S. Cl. .................. 604/8; 604/96.01; 604/100.01; 604/103.08; 604/919

(58) Field of Classification Search .................. 604/8, 604/96.01, 100.01, 100.02, 103.08, 912, 604/915, 919; D24/112
See application file for complete search history.

(56) References Cited

U.S. PATENT DOCUMENTS

| | | | | |
|---|---|---|---|---|
| 4,731,055 | A | | 3/1988 | Melinyshyn et al. ......... 604/100 |
| 5,217,024 | A | * | 6/1993 | Dorsey et al. ............... 600/571 |
| 5,993,382 | A | | 11/1999 | Pruitt, Sr. .................... 600/182 |
| 6,634,498 | B2 | * | 10/2003 | Kayerod et al. ............. 206/364 |
| 6,638,242 | B2 | * | 10/2003 | Wilson et al. ................. 604/43 |
| 2002/0019596 | A1 | * | 2/2002 | Eggers et al. ............... 600/564 |
| 2003/0120256 | A1 | * | 6/2003 | Lary et al. ................... 604/509 |
| 2007/0083154 | A1 | * | 4/2007 | Sauvageau ................... 604/73 |
| 2007/0100280 | A1 | * | 5/2007 | van Sloten et al. ....... 604/103.1 |

OTHER PUBLICATIONS

LeMaitre Vascular, "Pruitt-Inahara® Carotid Shunt", 2004, pp. 1-4.
LeMaitre Vascular, "Pruitt-Inahara/Inahara-Pruitt Carotid Shunts", 2002, pp. 1-4.

* cited by examiner

*Primary Examiner*—Tatyana Zalukaeva
*Assistant Examiner*—Michael G Bogart
(74) *Attorney, Agent, or Firm*—Greenberg Traurig, LLP; David J. Dykeman; Amy F. Mendel

(57) ABSTRACT

A shunt includes a first occlusion assembly and a second occlusion assembly. The first occlusion assembly includes a first occlusion fluid conduit that carries an inflation fluid from a fluid source to a first balloon of the shunt. The second occlusion assembly includes a second occlusion fluid conduit that carries an inflation fluid from a fluid source to a second balloon of the shunt. The first occlusion assembly includes a first color and the second fluid assembly includes a second color, distinct from the first color. The distinctive colorings of the first and second occlusion fluid conduits remain visible within an operative field during an endarterectomy procedure and allow a user to distinguish the first occlusion assembly from the second occlusion assembly during the procedure.

10 Claims, 4 Drawing Sheets

METHODS AND APPARATUS FOR VISUALLY DISTINGUISHING OCCLUSION ASSEMBLIES OF A SHUNT

BACKGROUND

In the process of atherosclerosis, as resulting from occlusive arterial disease, the inner lining of an artery receives deposits of fatty substances, cholesterol, and cellular waste products. The deposits form plaques within the artery that reduce or stop the flow of blood through the artery and that can dislodge from the arterial wall to cause a heart attack or stroke in a subject. One of the most common sites of occlusive arterial disease is the carotid artery. Health care professionals, such as surgeons, typically perform an endarterectomy within the carotid artery to remove the plaques and minimize the risk of stroke within the patient.

During an endarterectomy procedure, a surgeon typically clamps an occluded (or partially occluded) carotid artery both distal and proximal to the site of the occlusion and forms an incision (e.g., arteriotomy) in the artery at the occlusion site. To allow cerebral blood flow during the procedure, the surgeon utilizes a temporary shunt to allow blood to flow from the patient's heart to the patient's head while bypassing the operative site. Conventionally, the surgeon incises the carotid artery, places a shunting device (e.g., shunt) within the carotid artery, and orients the shunt proximally in the common carotid artery and distally past a bifurcation of the carotid artery (e.g., where the carotid artery divides into the internal carotid artery and the external carotid artery) into the internal carotid artery. The surgeon releases the distal and proximal clamps such that the shunt carries blood from the heart and to the internal carotid artery. The surgeon then accesses the artery, via the incision, and removes atherosclerotic plaques from the inner wall of the carotid artery.

In certain cases, the surgeon utilizes a balloon shunt as the shunting device during the endarterectomy procedure. FIG. 1 illustrates an example of a conventional balloon shunt 10. The balloon shunt 10 includes a conduit 12 having occlusive balloons 16, 14 located, respectively, at a first end 20 and a second end 18 of the conduit 12. The first occlusive balloon 16 connects to an inflation source 25 via a first fluid inlet conduit 26 and a first stopcock 28. The second occlusive balloon 14 connects to an inflation source 21 via a second fluid inlet conduit 22 and a second stopcock 24. Conventionally, the first occlusive balloon 16 conventionally has a fluid capacity of approximately 0.25 milliliters (ml) and an approximate 8 millimeter (mm) diameter at maximum liquid capacity (e.g., when inflated). Also, the second occlusive balloon 14 has a maximum fluid capacity of approximately 1.5 ml and an approximate 14 mm diameter at maximum fluid capacity (e.g., when inflated).

During operation, for example, the surgeon incises a carotid artery, inserts the second end 18 of the conduit 12 within a common carotid artery, and inserts the first end 20 of the conduit 12 into an internal carotid artery. The surgeon then inflates the balloons 14, 16 using an inflation fluid, such as a saline solution. Inflation of the balloons secures the shunt 10 to the carotid artery and occludes the carotid artery. The inflated balloons 14, 16 minimize the flow of blood within the arteriotomy site (e.g., cause the blood carried by the shunt 10 to bypass the arteriotomy site).

When the surgeon inserts the first occlusive balloon 16 of the shunt 10 within the internal carotid artery and inflates the balloon 16, the balloon creates pressure against an inner wall of the internal carotid artery, thereby securing the first occlusive balloon 16 within the internal carotid artery. The internal carotid artery, however, has a pressure sensitive structure or physiology that is susceptible to damage when exposed to relatively high or excessive pressures. As such, the conventional first fluid inlet conduit 26 includes a safety balloon 30 that limits the ability for a user to over-inflate the first occlusive balloon 16 and generate a relatively excessive pressure within the internal carotid artery.

For example, if a user over-inflates or over-pressurizes the first occlusive balloon 16 via the inflation source 25, the extra pressure diverts to the safety balloon 30, thereby inflating the safety balloon 30 and minimizing damage to the internal carotid artery. In the case where the safety balloon 30 inflates, the user removes fluid from the safety balloon 30 via the inflation source 25 to achieve an appropriate pressure within the first occlusive balloon.

The first fluid inlet conduit 26, in one arrangement, also includes a balloon sleeve 32 that operates in conjunction with the safety balloon 30. When the balloon sleeve 32 covers the safety balloon 30, the sleeve 32 limits expansion of the safety balloon 30 and minimizes transmission of fluid from the inflated first occlusive balloon 16 to the safety balloon 30.

For example, assume that the user inflates the first occlusive balloon 16 within the internal carotid artery. Further assume that the balloon sleeve 32 does not engage the safety balloon 30 (e.g., as shown in FIG. 1). In such an arrangement, during an endarterectomy procedure, fluid from the inflated first occlusive balloon 16 can travel from the first balloon 16, through the second fluid inlet conduit 26 and to the safety balloon 30, thereby inflating or expanding the safety balloon 30. As a result, the first occlusive balloon 16 deflates and becomes loose within the internal carotid artery, thereby leading to leakage of blood into the endarterectomy site. In the case where the balloon sleeve 32 engages or covers the safety balloon 30, the balloon sleeve 32 minimizes the ability for fluid from the inflated first occlusive balloon 16 to travel to, and expand, the safety balloon 30. The balloon sleeve 32, therefore, helps to minimize or prevent deflation of the inflated first occlusive balloon 16 during an endarterectomy procedure.

Additionally, in the balloon shunt 10, manufacturers conventionally shade the second occlusive balloon 14 and the second stopcock 24 with similar or corresponding colors 32 (e.g., a surface coloring or color coating) while maintaining the first occlusive balloon 16 and the first stopcock 28 with no detectable coloring. For example, a manufacturer forms the second balloon 14 and the second stopcock 24 each with a blue coloring and maintains the first occlusive balloon 16 and the first stopcock 28 with a substantially white shade.

The similar coloring 32 of the second occlusive balloon 14 and the second stopcock 24 identifies a correspondence between the second balloon 14 and the second stopcock 24. Therefore, during surgery, when the surgeon identifies a blue colored stopcock 24 within a surgical field (e.g., regardless of the positioning of the blue colored stopcock 24 relative to any other stopcocks present within the surgical field) and activates the inflation device 21 associated with the colored stopcock 24, the surgeon intuitively knows that such activation will inflate the blue colored second occlusive balloon 14 of the shunt device 10. Additionally, the similar coloring 32 of the second occlusive balloon 14 and the second stopcock 24 allows a surgeon to distinguish, within a surgical site, the second stopcock 24 and second occlusive balloon 14 from the conventionally uncolored first stopcock 28 and first occlusive balloon 16.

Also in the conventional balloon shunt 10, manufacturers include markings 36 on the shunt 10 to allow users to identify a correspondence between a particular stopcock and a particular balloon. For example, a manufacturer typically includes a first black band 36-1 on the conduit 12 in proximity to the second occlusive balloon 14. The manufacturer also includes a second black band 36-2 on the second stopcock 24. The presence of the bands 36-1, 36-2 on the shunt 10 allows a surgeon to identify the second stopcock 24 as corresponding to the second occlusive balloon 14 during a surgical procedure.

SUMMARY

Conventional mechanisms and techniques for identifying and distinguishing occlusion balloons of a shunt suffer from a variety of deficiencies.

For example, as indicated above, in the conventional balloon shunt 10, manufacturers configure the second occlusive balloon 14 and the second stopcock 24 with corresponding, similar colors 32 (e.g., a blue coloring). The corresponding coloring 32 of the second occlusive balloon 14 and the second stopcock 24 allows a surgeon to identify the second stopcock 24 as being coupled to (e.g., corresponding to) the second occlusive balloon 14. Therefore, when the surgeon identifies a blue colored stopcock 24 within a surgical field (e.g., regardless of the positioning of the blue colored stopcock 24 relative to any other stopcocks present within the surgical field) and activates the inflation device 21 associated with the colored stopcock 24, the surgeon intuitively knows that such activation will inflate the blue colored second occlusive balloon 14 of the shunt device 10.

During an endarterectomy procedure, however, the second occlusive balloon 14 inserts within a carotid artery such that the carotid artery visually obscures the second balloon 14 and the color 34 of the second balloon 14 from the user. As such, during an endarterectomy procedure, the user can forget the orientation of the second occlusive balloon 14 within the carotid artery (e.g., whether inserted within the common carotid artery or within the internal carotid artery). While the user knows that activation of the inflation mechanism 21 associated with the colored stopcock 24 inflates the blue colored second balloon 14, without the ability to detect an association of the colored stopcock 24 with a particular portion of the carotid artery (e.g., either the common carotid or the internal carotid artery), the user can accidentally over-inflate the second balloon 14 and potentially damage the carotid artery. Additionally, because the carotid artery visually obscures the second balloon 14 and the color 34 of the second balloon 14 the user can improperly or ineffectively activation the occlusion assemblies. As such, the balloon can accidentally deflate and cause leakage within the carotid artery.

For example, as indicated above, the internal carotid artery has a structure or physiology that is pressure sensitive and susceptible to damage when exposed to relatively high or excessive pressures. Also as indicated above, the second occlusive balloon 14 has a maximum inflation diameter of approximately 14 mm, substantially greater than the diameter of the internal carotid artery. Assume a case where a user inserts the colored second occlusive balloon 14 within the internal carotid artery such that the internal carotid artery visually obscures the second occlusive balloon 14. If the user inadvertently forgets of the orientation of the colored second occlusive balloon 14 within the internal carotid artery and, at a later time, operates the inflation mechanism 21 coupled to the colored stopcock 24 to provide maximum inflation to the colored second occlusive balloon 14, the user can exert a relatively high pressure on the wall of the internal carotid artery. In turn, the relatively high pressure produced by the second occlusive balloon 14 can damage or rupture the pressure sensitive internal carotid artery.

Also, as indicated above, manufacturers typically include a first black band 36-1 on the conduit 12 in proximity to the second occlusive balloon 14 and a second black band 36-2 on the second stopcock 24. The bands 36-1, 36-2 allow a surgeon to identify, during a surgical procedure, the second stopcock 24 as corresponding to the second occlusive balloon 14. The bands 36-1, 36-2, however, are relatively small and can be difficult to detect or can become obscured from the surgeon's field of view during surgery. As such, even with the presence of the relatively small bands 36-1, 36-2, a surgeon can still confuse a particular stopcock 24 or 28 as corresponding to a particular balloon 14 or 16 and can accidentally over-inflate one or both of the balloons 14, 16, thereby damaging the carotid artery.

Additionally, conventional mechanisms and techniques for utilizing a safety balloon and balloon sleeve of a shunt suffer from a variety of deficiencies.

As indicated above, the first fluid inlet conduit 26 of a conventional shunt 10 includes a safety balloon 30 that limits the ability for a user to over-inflate the first occlusive balloon 16 and generate a relatively excessive pressure within an internal carotid artery. Also as indicated above, when the balloon sleeve 32 engages or covers the safety balloon 30, the balloon sleeve 32 minimizes the ability for fluid from the inflated first occlusive balloon 16 to travel to, and expand, the safety balloon 30, thereby minimizing deflation of the inflated first occlusive balloon 16 during an endarterectomy procedure.

With respect to the safety balloon and the sheath 32, the safety balloon couples to the first fluid inlet conduit 26 where the first fluid inlet conduit 26 is typically formed of a transparent material, such as a polyurethane material. Additionally, the sleeve 32 is also typically formed of a transparent material, such as a polyurethane material. Typically, during a surgical procedure, a surgeon covers the safety balloon 30 with the sleeve 32 after the surgeon has inflated the first occlusive balloon 16. However, because both the first fluid inlet conduit 26 and the sleeve 32 are formed from a transparent material, the surgeon may not identify the presence of the sleeve 32 on the first fluid inlet conduit 26 and can then forget to cover the safety balloon 30 with the sleeve 32. As a result, fluid from the inflated first occlusive balloon 16 travels to the safety balloon 30, thereby inflating or expanding the safety balloon 30, deflating the first occlusive balloon 16, and causing leakage of blood into the endarterectomy site.

By contrast, embodiments of the present invention significantly overcome the described deficiencies and provide mechanisms and techniques for visually distinguishing the occlusion assemblies of a shunt. A shunt includes a first occlusion assembly and a second occlusion assembly. The first occlusion assembly includes a first occlusion fluid conduit that carries an inflation fluid from a fluid source to a first balloon of the shunt. The second occlusion assembly includes a second occlusion fluid conduit that carries an inflation fluid from a fluid source to a second balloon of the shunt. The first occlusion assembly includes a first color and the second fluid assembly includes a second color, distinct from the first color. The distinctive colorings of the first and second occlusion fluid conduits allow a user to distinguish the first occlusion assembly from the second occlusion assembly during an endarterectomy procedure. Furthermore, the distinct colorings of the each occlusion fluid conduit extend along a length of each conduit. The distinguishing and distinct coloring of each occlusion fluid conduit therefore, remains visible within an operative field (e.g., within a surgeon's sight path) during an endarterectomy procedure. As such, the surgeon can distinguish the first occlusion fluid conduit and the second occlusion fluid conduit during the endarterectomy procedure. Such a configuration of the shunt minimizes potential confusion of the first occlusion assembly with the second occlusion assembly. The configuration, therefore minimizes inadvertent, multiple activations of one of the occlusion assemblies and minimizes potential damage to a carotid artery. The configuration also minimizes improper or ineffective activation of one of the occlusion assemblies, thereby minimizing accidental deflation of the balloon and causing leakage within the carotid artery.

In one arrangement, a shunt apparatus includes a conduit having a first end and a second end, the conduit defining a lumen, a first occlusion assembly coupled to the conduit, and a second occlusion assembly coupled to the conduit. The first occlusion assembly has a first balloon disposed in proximity to the first end of the conduit and has a first occlusion fluid conduit in fluid communication with the first balloon where the first occlusion fluid conduit includes a first visual characteristic. The second occlusion assembly has a second balloon disposed at the second end of the conduit and has a second occlusion fluid conduit in fluid communication with the second balloon. The second occlusion fluid conduit includes a second visual characteristic distinct from the first visual characteristic. The distinctive colorings of the first and second occlusion fluid conduits allow a user to distinguish the first occlusion assembly from the second occlusion assembly during an endarterectomy procedure. Such a configuration of the shunt minimizes potential confusion of the first occlusion assembly with the second occlusion assembly and minimizes inadvertent, multiple activations of one of the occlusion assemblies that can potential damage a carotid artery. The configuration also minimizes improper or ineffective activation of one of the occlusion assemblies, thereby minimizing accidental deflation of the balloon and causing leakage within the carotid artery. In one arrangement, the first occlusion fluid conduit of the shunt apparatus includes an occlusion fluid conduit balloon and a sleeve configured to cover the occlusion fluid conduit balloon. The sleeve has a visual sleeve characteristic distinct from the first visual characteristic of the first occlusion fluid conduit. In the case where the user inflates a first balloon of the first occlusion assembly, such as to occlude an internal carotid artery, the visual difference between the sleeve and the first occlusion fluid conduit acts as a reminder to the surgeon to position the sleeve relative to the safety balloon to cover the safety balloon with the sleeve. As a result, the sleeve minimizes fluid within the inflated first balloon from traveling to the safety balloon, thereby inflating or expanding safety balloon and deflating the first balloon.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Embodiments of the present invention provide mechanisms and techniques for visually distinguishing the occlusion assemblies of a shunt. A shunt includes a first occlusion assembly and a second occlusion assembly. The first occlusion assembly includes a first occlusion fluid conduit that carries an inflation fluid from a fluid source to a first balloon of the shunt. The second occlusion assembly includes a second occlusion fluid conduit that carries an inflation fluid from a fluid source to a second balloon of the shunt. The first occlusion assembly includes a first color and the second fluid assembly includes a second color, distinct from the first color. The distinctive colorings of the first and second occlusion fluid conduits allow a user to distinguish the first occlusion assembly from the second occlusion assembly during an endarterectomy procedure. Furthermore, the distinct colorings of the each occlusion fluid conduit extend along a length of each conduit. The distinguishing and distinct coloring of each occlusion fluid conduit therefore, remains visible within an operative field (e.g., within a surgeon's sight path) during an endarterectomy procedure. As such, the surgeon can distinguish the first occlusion fluid conduit and the second occlusion fluid conduit during the endarterectomy procedure. Such a configuration of the shunt minimizes potential confusion of the first occlusion assembly with the second occlusion assembly. The configuration, therefore minimizes inadvertent, multiple activations of one of the occlusion assemblies and minimizes potential damage to a carotid artery.

Figure 1:
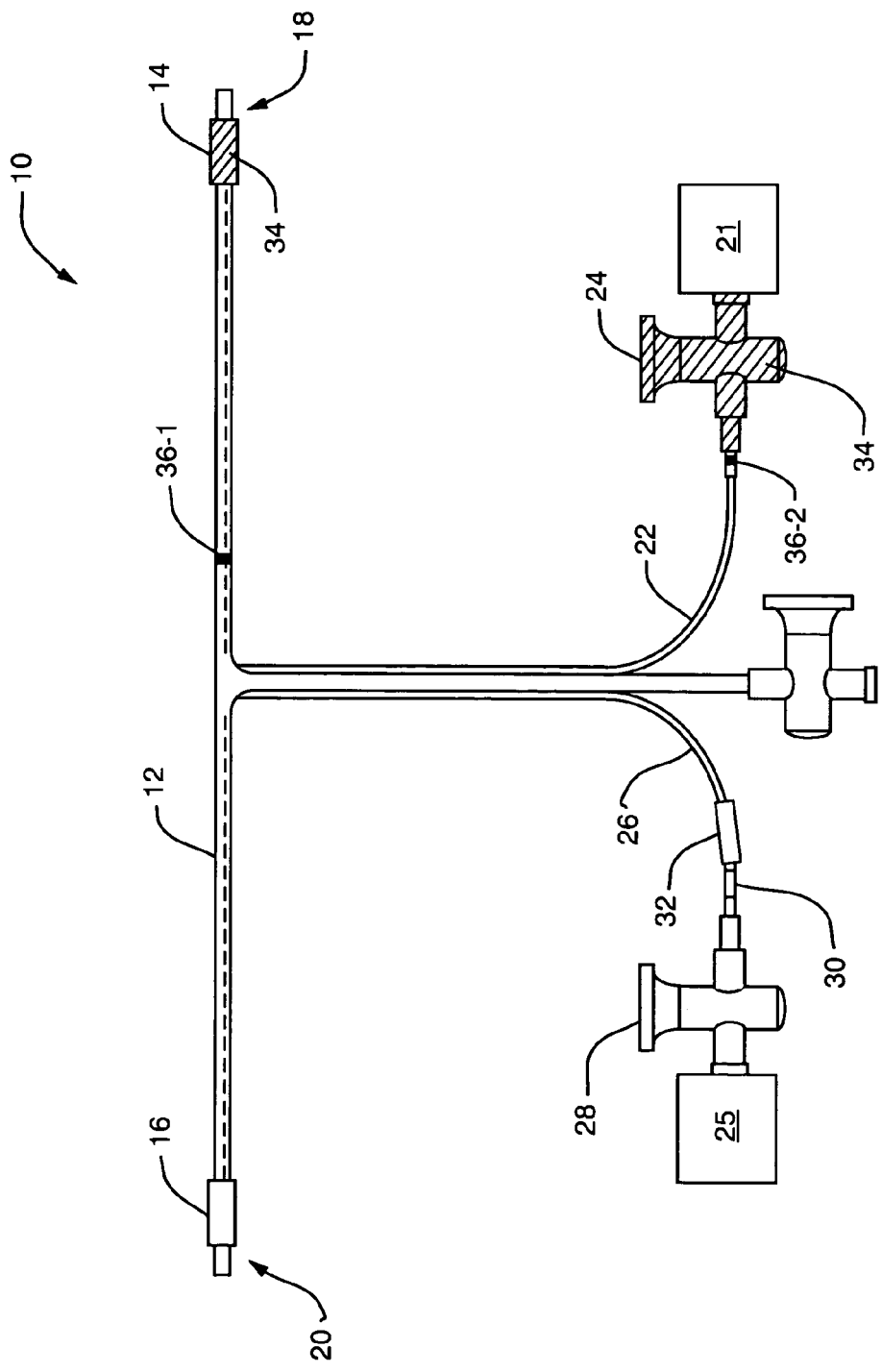
FIG. 1 illustrates a schematic representation of a prior art shunt.
Figure 2:
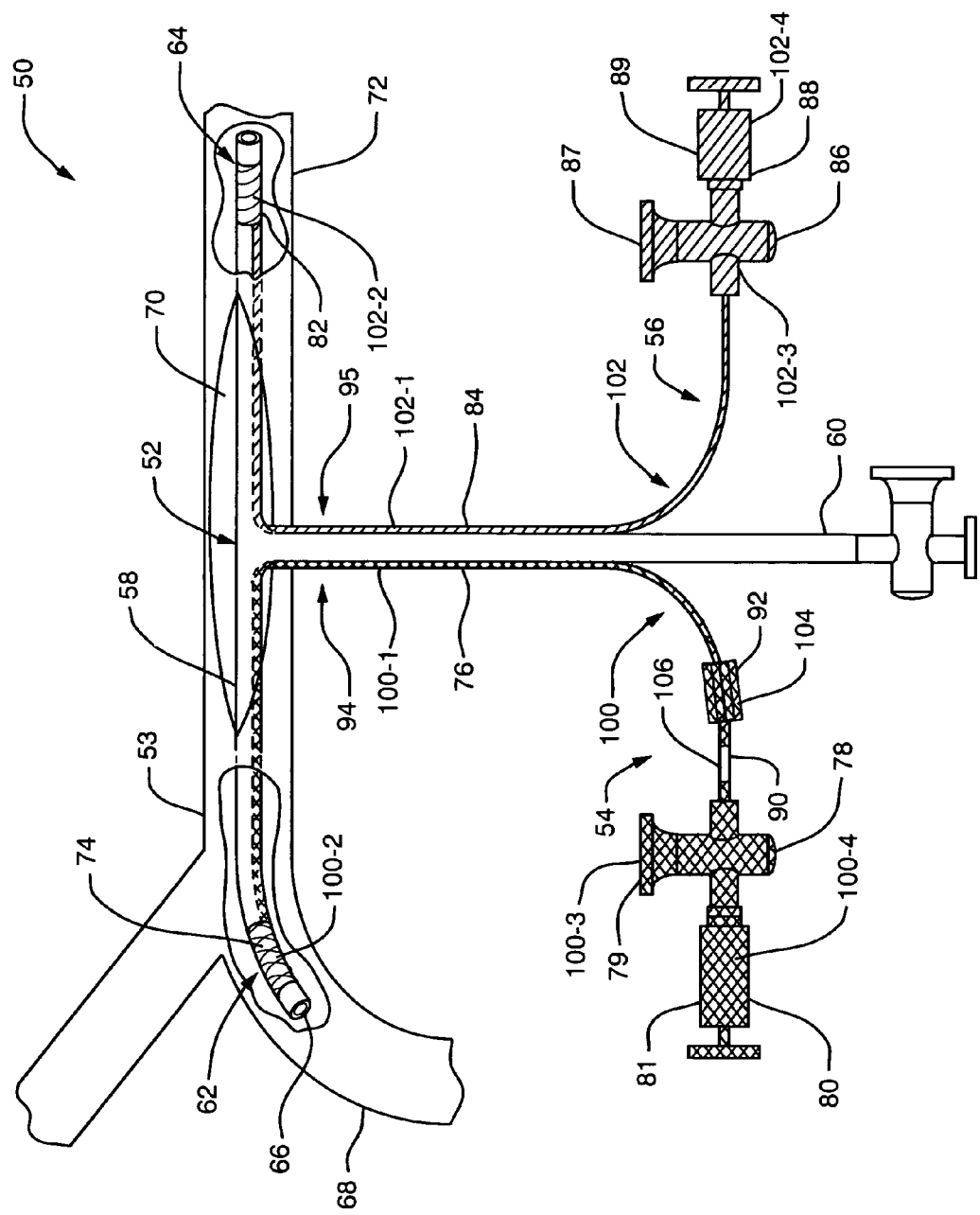
FIG. 2 illustrates a schematic representation of a shunt apparatus, according to embodiments of the invention.

FIG. 2 illustrates a shunt apparatus 50 having a conduit 52, a first occlusion assembly 54, and a second occlusion assembly 56. In one arrangement, the shunt apparatus 50 is configured as a balloon shunt to allow occlusion of a carotid artery 53 during an endarterectomy procedure and to allow blood to flow from the patient's heart to the patient's head while bypassing the operative endarterectomy site.

The conduit 52, in one arrangement, includes a transmission conduit 58 and an access conduit 60.

The transmission conduit 58 includes a first end 62 and a second end 64 and defines a lumen 66. For example, the transmission conduit 58 is configured as a tube or tube-like structure. During an endarterectomy procedure, for example, the first end 62 of the transmission conduit 58 is configured to insert within an internal carotid artery portion 68 of the carotid artery 53 via an incision 70 within the carotid artery 53. Also during the endarterectomy procedure, the second end 64 of the transmission conduit 58 is configured to insert within a common carotid artery portion 72 of the carotid artery 53 via the incision 70 within the carotid artery 53. The transmission conduit 58, therefore, allows blood to flow through the endarterectomy site, bypassing the incision, during an endarterectomy procedure.

The access conduit 60 defines a lumen and orients in fluid communication with, and substantially orthogonal to, the transmission conduit 58. The access conduit 60 is configured to allow a user to bypass a portion of the blood flowing through the transmission conduit 58.

The transmission conduit 58 and the access conduit 60, in one arrangement, are formed of a polyurethane material. For example, the polyurethane material is substantially transparent, thereby allowing a user to detect the presence of a fluid, such as blood, contained within the conduits 58, 60.

The first occlusion assembly 54 of the shunt apparatus 50 includes a first occlusion member, such as a first balloon 74 and a first occlusion fluid conduit 76 in fluid communication with (e.g., coupled to) the first balloon 74. The first occlusion fluid conduit 76 is configured to transmit a fluid to the first balloon 74, thereby causing the first balloon 74 to inflate and occlude a portion of a carotid artery, for example. The first occlusion assembly 54 also includes a first fluid access element 78, such as a valve or a stopcock 79, in fluid communication with the first occlusion fluid conduit 76 and a first fluid source or inflation source 80, such as a syringe 81, coupled to the first fluid access element 78. The first fluid access element 78 and the first fluid source 80 are configured to deliver fluid (e.g., a fluid causing the expansion or inflation of the first balloon 74) to the first occlusion fluid conduit 76 and first balloon 74.

The second occlusion assembly 56 of the shunt apparatus 50 includes a second occlusion member, such as a second balloon 82 and a second occlusion fluid conduit 84 in fluid communication with the second balloon 82. The second occlusion fluid conduit 84 is configured to transmit a fluid to the second balloon 82, thereby causing the second balloon 82 to inflate and occlude a portion of a carotid artery, for example. The second occlusion assembly 56 also includes a second fluid access element 86, such as a valve or a stopcock 87, in fluid communication with the second occlusion fluid conduit 84 and a second fluid source or inflation source 88, such as a syringe 89, coupled to the second fluid access element 86. The second fluid access element 86 and the second fluid source 88 are configured to deliver fluid (e.g., a fluid causing the expansion or inflation of the second balloon 82) to the second occlusion fluid conduit 76 and second balloon 82.

The first balloon 74 is disposed or oriented in proximity to the first end 62 of the conduit 52 while the second balloon 82 is disposed in proximity to the second end 64 of the conduit 52. In one arrangement, the first balloon 74 and the second balloon 82 are coupled to an exterior surface of the conduit 52, such as by a bonding (e.g., gluing) procedure. The first balloon 74, in one arrangement, has a fluid capacity of approximately 0.25 ml and an approximate 8 mm diameter when inflated to maximum fluid capacity. Also, the second balloon 82 has a fluid capacity of approximately 1.5 milliliters (ml) and an approximate 14 mm diameter inflated to maximum fluid capacity.

During operation, a user (e.g., surgeon) inserts the first end 62 of the conduit 52 within the internal carotid artery portion 68 of the carotid artery 53 and inserts the second end 64 of the conduit 52 within the common carotid artery portion 72 of the carotid artery 53. The user utilizes the first syringe 81 to inflate the first balloon 74 using a fluid, such as saline, contained within the syringe 81. Additionally, the user utilizes the second syringe 89 to inflate the second balloon 82 using a fluid, such as saline, contained within the syringe 89. The fluid from the first syringe 81 travels through the first stopcock 79 and through the corresponding occlusion fluid conduit 76 to expand the first balloon 74. The user then closes the first stopcock 79 to maintain fluid pressure within the first balloon 74 and the first occlusion fluid conduit 76. Fluid from the second syringe 89 travels through the second stopcock 87 and through the corresponding occlusion fluid conduit 84 to expand the second balloon 82. The user then closes the second stopcock 87 to maintain fluid pressure within the second balloon 82 and the second occlusion fluid conduit 84. As the first and second balloons 74, 82 expand, the balloons 74, 82 secure the shunt 52 to the carotid artery 68 and limit or block flow of blood through the carotid artery 53, thereby allowing the blood to flow through the lumen 66 of the transmission conduit 52 from the heart to the brain of a patient undergoing the endarterectomy procedure.

The first occlusion conduit 76 of the shunt apparatus 50 also includes an occlusion fluid conduit balloon or safety balloon 90 and a sleeve 92 configured to cover the safety balloon 90. As indicated above, if a user over-inflates or over-pressurizes the first balloon 74, the extra pressure diverts to the safety balloon 90, thereby minimizing damage to the internal carotid artery 68. In the case where the balloon sleeve 92 engages or covers the safety balloon 90, the balloon sleeve 92 minimizes the ability for fluid from the inflated first balloon 74 to travel to, and expand, the safety balloon 90. The balloon sleeve 92, therefore, helps to minimize or prevent deflation of the inflated first balloon 74 during an endarterectomy procedure.

As shown in FIG. 2, components of the first occlusion assembly 54 include a first visual characteristic 100 (e.g., as indicated by a grid pattern) and components of the second occlusion assembly 56 include a second visual characteristic 102 (e.g., as indicated by a hash mark pattern), distinct from the first visual characteristic 100. In one arrangement, the first and second visual characteristics 100, 102 are defined as distinct colors or hues applied to or associated with components of the respective assemblies 54, 56. For example, during the manufacturing process, assume a manufacturer forms components of the first occlusion assembly 54 as transparent or as having a white (e.g., non-colored) hue. The manufacturer then forms components of the second occlusion assembly 56 as having a color or hue distinct from the transparent or white hue of the first occlusion assembly 54. For example the manufacturer forms the components of the second occlusion assembly 56 as having blue color or hue. By providing particular and separate colors (e.g., visual characteristics) to components of the first occlusion assembly 54 and the second occlusion assembly 56, a manufacturer allows a surgeon to distinguish, in a comparison of similar components, the components of the first occlusion assembly 54 from the components of the second occlusion assembly during an endarterecomy procedure. As such, the manufacturer minimizes the potential for the surgeon to confuse the first occlusion assembly 54 with the second occlusion assembly 56 and inadvertently inflate the same balloon (e.g., either the first balloon 74 or the second balloon 82) multiple, consecutive times, thereby over-pressurizing one of the balloons 74, 82 and potentially damaging the carotid artery 53.

As will be described below, a manufacturer can form one or more of the components of the first occlusion assembly 54 and the second occlusion assembly 56 with distinct visual characteristics or colors.

In one arrangement, the manufacturer configures the first occlusion fluid conduit 76 of the first occlusion assembly 54 with a first visual characteristic 100-1 and configures the second occlusion fluid conduit 84 with a second visual characteristic 102-1, distinct from the first visual characteristic 100-1. For example, the manufacturer forms the first occlusion fluid conduit 76 as a transparent conduit (e.g., having no color 100-1) and forms the second occlusion fluid conduit 84 as having a blue color 102-1. As such, the distinctive colorings 100-1, 102-1 of the first 76 and second 84 occlusion fluid conduits allow a user to distinguish the first occlusion assembly 54 from the second occlusion assembly 56 during an endarterectomy procedure.

In one arrangement, the coloring 100-1, 102-1 of each occlusion fluid conduit 76, 84 extends along a length of each conduit 76, 84, from the stopcocks 79, 87 to the balloon 74, 82 respectively. The distinguishing and distinct coloring 100-1, 100-2 of each occlusion fluid conduit 76, 84, therefore, remains within a surgeon's sight path during an endarterectomy procedure and are substantially visible by the surgeon during the procedure. As such, the surgeon can distinguish the first occlusion fluid conduit 76 and the second occlusion fluid conduit 84, and therefore corresponding occlusion assemblies 54, 56, during the endarterectomy procedure.

Additionally, with the coloring 100-1, 102-1 of each occlusion fluid conduit 76, 84 extending along a length of each conduit 76, 84, from the respective stopcocks 79, 87 to the respective balloons 74, 82 the occlusion fluid conduits 76, 84 allow the user to detect a correspondence between the respective stopcocks 79, 87 and the respective balloons 74, 82. For example, as indicated in FIG. 2, the second occlusion fluid conduit 84 has a second visual characteristic (e.g., blue color) 102-1 that extends along the conduit 84 from the second stopcock 87 to the second balloon 82. A portion of the second occlusion fluid conduit 84 orients within the second end 64 of the transparent transmission conduit 58. During operation, a user views the distinct coloring 102-1 of the second occlusion fluid conduit 84 from the second stopcock 87, through the transparent transmission conduit 52, to the second balloon 82. The distinct coloring 102-1 of the second occlusion fluid conduit 84 (relative to the coloring 100-1 of the first occlusion fluid conduit 76), therefore, provides a user with a direct visual link between the second stopcock 87 and the second balloon 82 and allows the user to detect a correspondence between the second stopcock 87 and the second balloon 82. As such, the coloring 100-1, 102-1 of each occlusion fluid conduit 76, 84 extending along a length of each conduit 76, 84 minimizes the potential for the surgeon to confuse the first occlusion assembly 54 with the second occlusion assembly 56 during an endarterectomy procedure.

In one arrangement, the first balloon 74 is configured with a first visual characteristic 100-2 and the second balloon 82 is configured with second visual characteristic 102-2 distinct from the first visual characteristic 100-2. For example, the manufacturer forms the first balloon 74 as having a non-colored or white shade 100-2 and forms the second balloon 82 as having a blue color 102-2. By providing the balloons 74, 82 with distinct visual characteristics or colors, as used in conjunction with the colored 100-1 first occlusion fluid conduit 76 and the colored 102-1 second occlusion fluid conduit 84, respectively, the manufacturer allows the user or surgeon to further distinguish the first occlusion assembly 54 from the second occlusion assembly 56. As such, the distinct coloring helps to minimize potential confusion between the assemblies 54, 56 on the part of the surgeon during an endarterectomy procedure.

In one arrangement, the manufacturer configures the first fluid access element 78, such as the first stopcock 79, with a first visual characteristic 100-3 and configures the second fluid access element 86, such as the second stopcock 87, with a second visual characteristic 102-3 distinct from the first visual characteristic 100-3 of the first fluid access element 78. For example, in one arrangement, the first stopcock 79 includes a white hue or shading 100-3 and the second stopcock 87 includes a blue coloring 102-3. Additionally, in one arrangement, the manufacturer configures the first fluid source 80, such as the first syringe 81, with a first visual characteristic 100-4 and configures the second fluid source 88, such as the second syringe 89 with a second visual characteristic 102-4 distinct from the first visual characteristic 100-4. For example, in one arrangement, the first syringe 81 includes a white hue or shading 100-4 and the second syringe 89 includes a blue coloring 102-4. By providing the first 79 and second 87 stopcocks with distinct visual characteristics or colors 100-3, 102-3 and by providing the first 81 and second 89 syringes with distinct visual characteristics or colors 100-4, 102-4, as used in conjunction with the colored 100-1 first occlusion fluid conduit 76 and the colored 102-1 second occlusion fluid conduit 84, the manufacturer allows the user or surgeon to further distinguish the first occlusion assembly 54 from the second occlusion assembly 56. As such, the distinct coloring helps to minimize potential confusion between the assemblies 54, 56 on the part of the surgeon during an endarterectomy procedure.

As indicated above, the first occlusion conduit 76 of the shunt apparatus 50 includes the safety balloon 90 and sleeve 92. In one arrangement, the sleeve 92 has a visual sleeve characteristic 104 distinct from the first visual characteristic 100-1 of the first occlusion fluid conduit 76. For example, assume the first occlusion fluid conduit 76 is configured as a transparent polyurethane material (e.g., having no color 100-1) and the sleeve or sheath 92 is formed with a purple coloring 104. The purple coloring 104 of the sleeve 92 visually distinguishes the sleeve 92 from the transparent first occlusion fluid conduit 76. During an endarterectomy procedure, the visual difference between the sleeve 92 and the first occlusion fluid conduit 76 allows the surgeon to identify the location of the sleeve 92 on the first occlusion fluid conduit 76 and determine positional relation between the sleeve 92 and the safety balloon 90. In the case where the user inflates the first balloon 74 to occlude the internal carotid artery 68, the visual difference between the sleeve 92 and the first occlusion fluid conduit 76 acts as a reminder to the surgeon to position the sleeve 92 relative to the safety balloon 90 to cover the safety balloon 30 with the sleeve 32. As a result, the sleeve 92 minimizes fluid within the inflated first balloon 74 from traveling to the safety balloon 90, thereby inflating or expanding safety balloon 90 and deflating the first balloon 74.

Figure 3:
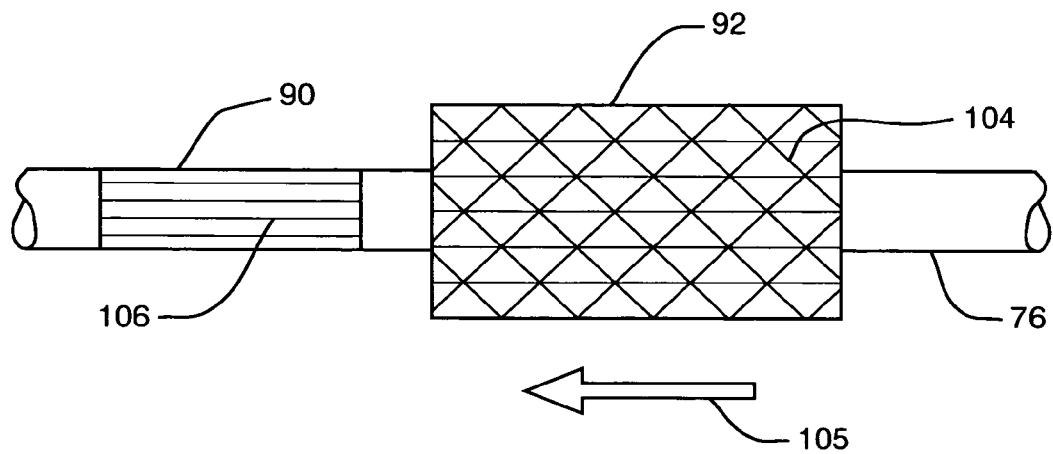
FIG. 3 illustrates an arrangement of a safety balloon and sleeve of the shunt apparatus of FIG. 1 in an unengaged state.
Figure 4:
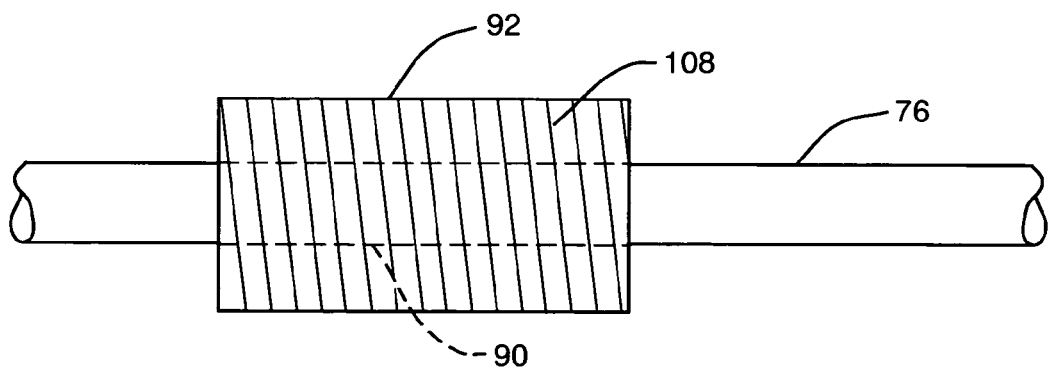
FIG. 4 illustrates an arrangement of the safety balloon and sleeve of FIG. 4 in an engaged state.

As shown in FIGS. 3 and 4, in one arrangement, when the user covers the safety balloon 90 with the sleeve 92, an optical combination of the sheath color 104 and a balloon color 106 produce an indication color 108, distinct from the balloon color 106 and the sleeve color 104.

For example, as shown in FIG. 3, a manufacturer forms the sleeve 92 from a translucent polyurethane material having a sleeve color 104, such as a translucent yellow color 104. Additionally, the manufacturer utilizes, as part of the first occlusion conduit 76, a safety balloon 90 having a red hue or color 106. In such an example, when a user engages 105 the sleeve 92 with the safety balloon 90, as shown in FIG. 4, the optical combination of the safety balloon 90 and the sleeve 92 (e.g., as caused by the translucent yellow color 104 of the sleeve 92) produces an orange color 108 (e.g., an indication color). The resulting orange indication color 108 provides a notification to the surgeon that the sleeve 92 has properly engaged the safety balloon 90. By contrast, using the same example, in the event the surgeon does not view an orange indication color 108 on, or relative to, the first occlusion conduit 76, absence of the orange indication color 108 can remind the surgeon to cover the safety balloon 90 with the sleeve 92 to minimize the potential for deflation of the first balloon 74 during an endarterectomy procedure.

As indicated above, the manufacturer provides distinct visual indicators to similar components of the occlusion assemblies (e.g., the manufacturer assigns no color 100-1 to the first occlusive fluid conduit 76 and assigns a blue color 102-1 to the second occlusive fluid conduit 84) in order to allow a surgeon to distinguish similar components from each other (e.g., to distinguish the first stopcock 79 from the second stopcock 87) in an endarterectomy procedure. In one arrangement, the manufacturer assigns a common visual grouping characteristic, such as a common color, to the components of each particular occlusion assembly 54, 56. As such, the manufacturer allows a user to identify a component as belonging to, or as being associated with, a particular occlusion assembly 54, 56 based upon the assigned color of the component.

Returning to FIG. 2, for example, the manufacturer configures the components (e.g., the first balloon 74, first occlusion fluid conduit 76, first fluid access element 78, and first fluid source 80) of the first occlusion assembly 54 with a first common visual grouping characteristic 94, such as a red color (e.g., red surface coloring or red hue). The manufacturer also, for example, configures the components (e.g., the second balloon 82, second occlusion fluid conduit 84, second fluid access element 86, and second fluid source 88) of the second occlusion assembly 56 with a second common visual grouping characteristic 95, such as a blue color (e.g., blue surface coloring or blue hue). Because the components 74, 76, 78, 80 within the first occlusion assembly 54 have the same or relatively similar red coloring, during operation, a user can visually identify the components 74, 76, 78, 80 as belonging to the first occlusion assembly 56 based upon the red coloring of the components. Additionally, because each of the components 82, 84, 86, 88 within the second occlusion assembly 56 have the same or relatively similar blue coloring, during operation, a user can visually identify the components 82, 84, 86, 88 as belonging to the second occlusion assembly 56 based upon the blue color of the components.

In one arrangement, the first common visual grouping characteristic 94 of the first occlusion assembly 54 and the distinct second common visual grouping characteristic 95 of the second occlusion assembly 56 minimizes the probability of the user or surgeon confusing the first occlusion assembly 54 with the second occlusion assembly 56 during a procedure. As such, the distinct common visual grouping characteristics 94, 95 of the components of the assemblies 54, 56 minimizes the probability of the surgeon inadvertently activating either the first occlusion assembly 54 or the second occlusion assembly 56 more than two consecutive times during an endarterectomy procedure, thereby potentially damaging a carotid artery 53.

As indicated above, by assigning distinct common visual grouping characteristics 94, 95 to the components of each of the occlusion assemblies 54, 56 (e.g., all components of the first occlusion assembly 54 have a red color and all components of the second occlusion assembly 56 have a blue color), the manufacturer identifies a component as belonging to a particular occlusion assembly 54, 56. In one arrangement, the manufacturer utilizes the common visual grouping characteristics 94, 95 of the shunt 50 to ensure proper orientation and insertion of the shunt 50 within the carotid artery 53.

For example, as indicated above, the first balloon 74 has a fluid capacity of approximately 0.25 ml and an approximate 8 mm diameter when inflated. The second balloon 82 has a maximum fluid capacity of approximately 1.5 ml and an approximate 14 mm diameter when inflated. The given geometries of the first balloon 74 and the second balloon 82 and the geometries of the common 72 and internal 68 carotid arteries, therefore, require a user to insert and expand the second balloon 82 within the common carotid artery 72 and insert and expand the relatively smaller first balloon 74 within the relatively smaller internal carotid artery 68.

In order to ensure proper orientation of the occlusion assemblies 54, 56 relative to the carotid artery 53 and to ensure a user utilizes the appropriate balloon (e.g., the first balloon 74) within an appropriate portion of the carotid artery 53 (e.g., the internal carotid artery 68), the manufacturer assigns a coloring convention to the common carotid artery 72 and the internal carotid artery 68 corresponding to the distinct, common visual grouping characteristics 94, 95 of the occlusion assemblies 54, 56. By correlating the common visual grouping characteristics 94, 95 of the components with a coloring convention assigned to the carotid artery 53, the user minimizes improperly orienting and applying the shunt 50 to the carotid artery 53.

Figure 5:
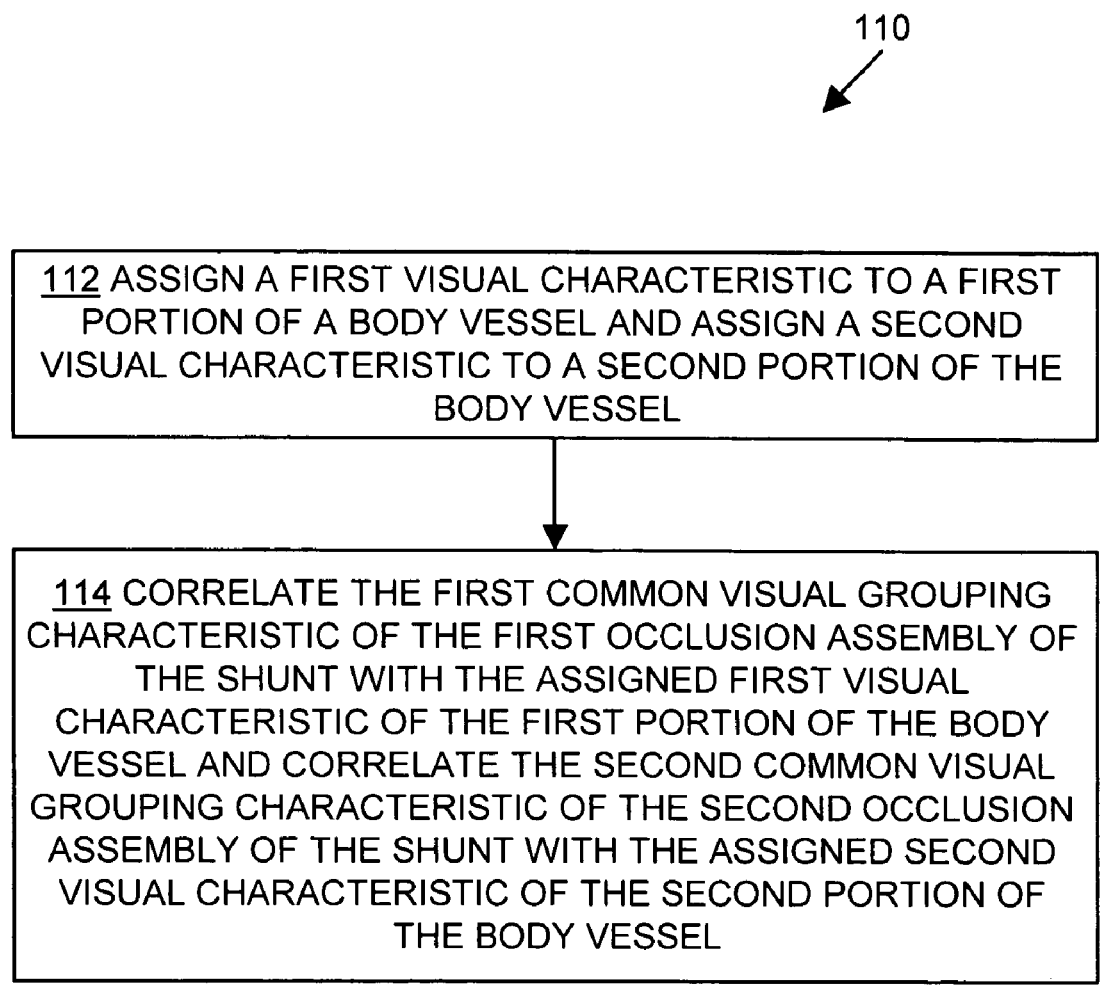
FIG. 5 is a flowchart of a procedure performed by a surgeon when using the shunt apparatus of FIG. 1.

FIG. 5 is a flowchart 110 of a procedure for inserting a shunt apparatus 50 within a body vessel, such as a carotid artery 53, while maintaining the proper orientation of the occlusion assemblies 54, 56 relative to the body vessel.

In step 112 a manufacturer assigns a first visual characteristic to a first portion of a body vessel and assigns a second visual characteristic to a second portion of the body vessel. In one arrangement, the manufacturer assigns a first visual characteristic, such as a color, to the internal carotid artery 68 and assigns a second visual characteristic, such as a color, to the common carotid artery 72.

For example, assume the manufacturer configures the components of the first occlusion assembly 54 of the balloon shunt 50 as having a common red shade 94 and configures the components of the second occlusion assembly 56 as having a common blue shade 95. In order to ensure that during a surgical procedure, the user inserts the relatively larger second balloon 82 within the common carotid artery 72 and inserts the relatively smaller first balloon 74 within the internal carotid artery 68, the manufacturer assigns the internal carotid artery a "red" designation and assigns the common carotid artery a "blue" designation. As such, the manufacturer creates a correspondence between the internal carotid artery 68 and the color "red" and between the common carotid artery 72 the color "blue".

In step 114, the user correlates the first common visual grouping characteristic 94 (e.g., common color) of the first occlusion assembly 54 of the shunt 50 with the assigned first visual characteristic of the first portion of the body vessel. The user also correlates the second common visual grouping characteristic 95 (e.g., common color) of the second occlusion assembly 56 of the shunt 50 with the assigned second visual characteristic of the second portion of the body vessel.

For example, with the aforementioned assigned coloring convention relative to the internal 68 and common 72 carotid arteries, the user matches the common red colored 94 first occlusion assembly 54 to the internal carotid artery 68 and matches the common blue colored 95 second occlusion assembly 56 to the common carotid artery 72. By relating the assigned "red" coloring convention of the internal carotid artery 68 and the assigned "blue" coloring convention of the common carotid artery 72 with the corresponding common colorings 94, 95 of the occlusion assemblies 54, 56, the user ensures proper operation of the shunt 50 within the carotid artery 53. Use of the assigned coloring convention minimizes accidental reversal of the shunt 50 relative to the carotid artery 53 (e.g., the red first balloon 74 inserted within the common carotid artery 72 and the blue second balloon 82 inserted within the internal carotid artery 68) during an endarterectomy procedure. In turn, by utilizing the assigned convention, the user minimizes potential damage to the internal carotid artery 68 caused by the second balloon 82 (e.g., as caused by the user maximally inflating the second balloon 82 to an approximate 14 mm diameter within the internal carotid artery 68).

The assigned coloring convention also allows a user to recognize the proper orientation of the shunt 50, relative to the carotid artery 53, after application of the shunt to a carotid artery 53 and during the endarterectomy procedure. For example, assume during an endarterectomy procedure, second balloon 82 inadvertently exits or "pops out" from the common carotid artery 72 during an endarterectomy procedure. In such a case, the surgical site fills with blood from the common carotid artery 72, thereby visually obscuring the surgical site and limiting the ability of the surgeon to detect the source of the blood, either the common carotid artery or the internal carotid artery. Further assume that, upon insertion, the surgeon related the assigned coloring convention of the common carotid artery 72 and the internal carotid artery 68 with the corresponding coloring 94, 95 of the occlusion assemblies 54, 56. In such a case, when the surgeon visually inspects the free end (e.g., the end not inserted within the carotid artery 53) of the shunt 50 and detects the blue coloring 95 of the second balloon 82, the surgeon correlates the blue coloring 95 of the second balloon 82 with the color "blue" assigned to the common carotid artery 72. Based upon the correlation, the surgeon can reinsert the second balloon 82 within the common carotid artery 72 in a relatively short time span, thereby minimizing blood loss to the patient.

While this invention has been particularly shown and described with references to preferred embodiments thereof, it will be understood by those skilled in the art that various changes in form and details may be made therein without departing from the spirit and scope of the invention as defined by the appended claims.

For example, as indicated above, the first visual characteristic 100 of the first occlusion assembly 54 and the second visual characteristic 102 of the second occlusion assembly 56 are defined as distinct colors or hues applied to or associated with components of the respective assemblies 54, 56. Such definition is by way of example only. In one arrangement, the first visual characteristic 100 of the first occlusion assembly 54 and the second visual characteristic 102 of the second occlusion assembly 56 are defined as distinct patterns, such as applied to the surfaces of the components associated with each of the occlusion assemblies 54, 56. For example, in one arrangement, the first stopcock 77, the first occlusion fluid conduit 76, and the first balloon 74 are configured with a common polka dot pattern, such as printed on the surface of the components 77, 76, 74, while the second stopcock 87, the second occlusion fluid conduit 84, and the second balloon 86 are configured with a common striped pattern, such as printed on the surface of the components 87, 84, 82.

Additionally, the first common visual grouping characteristic 94 and the second common visual grouping characteristic 95 are defined as colors applied to the components of the respective occlusion assemblies 54, 56. Such definition is by way of example only. In one arrangement, the first common visual grouping characteristic 94 of the first occlusion assembly 54 and the second common visual grouping characteristic 95 of the second occlusion assembly 56 are defined as distinct patterns, such as applied to the surfaces of the components associated with each of the occlusion assemblies 54, 56.

As indicated above, components of the first occlusion assembly 54 include a first visual characteristic 100 and components of the second occlusion assembly 56 include a second visual characteristic 102, distinct from the first visual characteristic 100. As indicated in the example above, a manufacturer configures the first occlusion fluid conduit, as having a white shade 100 and configures the second occlusion fluid conduit, as having a blue color 102. In the additional examples listed above, the manufacturer configures the other components of the first occlusion assembly 54 (e.g., the first balloon, first stopcock, and first syringe) as having a white shade 100, similar to the shade of the first occlusion fluid conduit. Also in the examples listed above, the manufacturer configures the other components of the second occlusion assembly 56 (second balloon, second stopcock, and second syringe) as having a blue shade 100, similar to the shade of the second occlusion fluid conduit 84, and distinct from the white shade of the first occlusion assembly components. Such description is provided by way of example only. In one arrangement, when the manufacturer provides first visual characteristic to the components of the first occlusion assembly 54 and a second, distinct visual characteristic to the components of the second occlusion assembly 56, the manufacturer does not necessarily use a single color or hue for all of the components of a particular occlusion assembly 54, 56.

For example, the manufacturer can assign the primary colors to the components of the first occlusion assembly 54 (e.g., red for the first balloon 72, blue for the first occlusion fluid conduit 76, and yellow for the first stopcock 79 and first syringe 81) and can assign the secondary colors to the components of the second occlusion assembly (e.g., orange for the second balloon 82, green for the second occlusion fluid conduit 84, and purple for the second stopcock 87 and second syringe 89). Such an arrangement allows user to distinguish individual components of the occlusion assemblies 54, 56 without requiring a common visual grouping characteristic assigned to either the first occlusion assembly 54 or the second occlusion assembly 56.

In another example, FIG. 2 illustrates a shunt 50 as having a first occlusion assembly 54 (e.g., a first balloon 74 coupled to a first occlusion fluid conduit 76) and a second occlusion assembly 56 (e.g., a second balloon 72 coupled to a second occlusion fluid conduit 84) where, at least, the first occlusion fluid conduit 76 and the second occlusion fluid conduit 84 have relatively distinctive visual characteristics or colors. Such illustration is by way of example only. In one arrangement, the shunt 50 includes three or more occlusion assemblies. In such an arrangement, the occlusion fluid conduit of each occlusion assembly is configured with distinctive visual characteristics or colors (e.g., distinctive relative to each other). As such, a user can distinguish each occlusion assembly during a surgical procedure.

As indicated above, in one arrangement, the sleeve 92 has a visual sleeve characteristic 104 distinct from the first visual characteristic 100-1 of the first occlusion fluid conduit 76. For example, assume the first occlusion fluid conduit 76 is configured as a transparent polyurethane material (e.g., having no color 100-1) and the sleeve or sheath 92 is formed with a purple coloring 104. The purple coloring 104 of the sleeve 92 visually distinguishes the sleeve 92 from the transparent first occlusion fluid conduit 76. Such description is by way of example only. In one arrangement, the sleeve 92 includes a geometric pattern as visual sleeve characteristic 104 where the pattern is distinct from a pattern (e.g., the first visual characteristic 100-1) of the first occlusion fluid conduit 76.

What is claimed is:

1. A shunt apparatus comprising:
   a conduit having a first end and a second end, the conduit defining a lumen;
   a first occlusion assembly coupled to the conduit, the first occlusion assembly having a first balloon disposed in proximity to the first end of the conduit and a first occlusion fluid conduit in fluid communication with the first balloon, the first occlusion fluid conduit having a first visual characteristic; and
   a second occlusion assembly coupled to the conduit, the second occlusion assembly having a second balloon disposed at the second end of the conduit and a second occlusion fluid conduit in fluid communication with the second balloon, the second occlusion fluid conduit having a second visual characteristic distinct from the first visual characteristic, wherein the first occlusion fluid conduit comprises an occlusion fluid conduit balloon and a sleeve configured to cover the occlusion fluid conduit balloon, the sleeve having a visual sleeve characteristic distinct from the first visual characteristic of the first occlusion fluid conduit, wherein occlusion fluid conduit balloon comprises a balloon color distinct from a sleeve color of the sleeve, the balloon color of the occlusion fluid conduit balloon and the sleeve color of the sleeve configured to optically combine to produce an indication color, distinct from the balloon color and the sleeve color.

2. The shunt apparatus of claim 1 wherein the first visual characteristic comprises a first color and the second visual characteristic comprises a second color distinct from the first color.

3. The shunt apparatus of claim 1 wherein the first balloon is configured with a first visual characteristic and the second balloon is configured with a second visual characteristic distinct from the first visual characteristic.

4. The shunt apparatus of claim 1 wherein:
the first occlusion assembly comprises a first fluid access element in fluid communication with the first occlusion fluid conduit, the first fluid access element configured to couple to a first fluid source and the first fluid access element having a first visual characteristic; and
the second occlusion assembly comprises a second fluid access element in fluid communication with the second occlusion fluid conduit, the second fluid access element configured to couple to a second fluid source and the second fluid access element having a second visual characteristic distinct from the first visual characteristic.

5. The shunt apparatus of claim 4 wherein at least one of the first fluid access element and the second fluid access element are chosen from the group consisting of a stopcock and a valve.

6. The shunt apparatus of claim 4 comprising:
a first fluid source coupled to the first fluid access element, the first fluid source having a first visual characteristic; and
a second fluid source coupled to the second fluid access element, the second fluid source having a second visual characteristic distinct from the first visual characteristic.

7. The shunt apparatus of claim 6 wherein at least one of the first fluid source and the second fluid source comprises a syringe.

8. The shunt apparatus of claim 1, wherein:
the conduit is formed from a substantially transparent material;
the first occlusion fluid conduit is at least partially disposed within the conduit such that the first visual characteristic of the first occlusion fluid conduit is configured to be visible through the conduit when the first balloon is disposed within a carotid artery; and
the second occlusion fluid conduit is at least partially disposed within the conduit such that the second visual characteristic of the second occlusion fluid conduit is configured to be visible through the conduit when the second balloon is disposed within the carotid artery.

9. The shunt apparatus of claim 1, wherein:
the conduit includes a transmission conduit and an access conduit, the access conduit being in fluid communication with, and substantially orthogonal to, the transmission conduit, the transmission conduit having the first balloon disposed in proximity to a first end of the transmission conduit and the second balloon disposed in proximity to a second end of the transmission conduit;
the first occlusion fluid conduit being partially disposed within the transmission conduit and being partially disposed external to the access conduit, the first occlusion fluid conduit configured to be visible through the transmission conduit in a surgical field when the first balloon is disposed within a carotid artery; and
the second occlusion fluid conduit being partially disposed within the transmission conduit and being partially disposed external to the access conduit, the second occlusion fluid conduit configured to be visible in a surgical field when the second balloon is disposed within the carotid artery.

10. A shunt apparatus comprising:
a conduit formed from a substantially transparent material having a transmission conduit and an access conduit, the access conduit being in fluid communication with, and substantially orthogonal to, the transmission conduit,
a first occlusion assembly carried by the conduit, the first occlusion assembly having a first balloon disposed in proximity to a first end of the transmission conduit and a first occlusion fluid conduit in fluid communication with the first balloon, the first occlusion fluid conduit and the first balloon having a first visual characteristic;
a first fluid access element in fluid communication with the first occlusion fluid conduit, the first fluid access element configured to couple to a first fluid source and the first fluid access element having the first visual characteristic;
a second occlusion assembly carried by the conduit, the second occlusion assembly having a second balloon disposed at a second end of the transmission conduit, the second end opposing the first end, and a second occlusion fluid conduit in fluid communication with the second balloon, the second occlusion fluid conduit and the second balloon having a second visual characteristic distinct from the first visual characteristic;
a second fluid access element in fluid communication with the second occlusion fluid conduit, the second fluid access element configured to couple to a second fluid source and the second fluid access element having the second visual characteristic distinct from the first visual characteristic;
the first occlusion fluid conduit being partially disposed within the transmission conduit and being partially disposed external to the access conduit, the first occlusion fluid conduit configured to be visible through the transmission conduit in a surgical field when the first balloon is disposed within a carotid artery; and
the second occlusion fluid conduit being partially disposed within the transmission conduit and being partially disposed external to the access conduit, the second occlusion fluid conduit configured to be visible in a surgical field when the second balloon is disposed within the carotid artery,
wherein the first occlusion fluid conduit comprises an occlusion fluid conduit balloon and a sleeve configured to cover the occlusion fluid conduit balloon, the sleeve having a visual sleeve characteristic distinct from the first visual characteristic of the first occlusion fluid conduit,
wherein occlusion fluid conduit balloon comprises a balloon color distinct from the sleeve color of the sleeve, the balloon color of the occlusion fluid conduit balloon and the sleeve color of the sleeve configured to optically combine to produce an indication color, distinct from the balloon color and the sleeve color.

* * * * *